US012605567B2

(12) United States Patent
Liu et al.

(10) Patent No.: US 12,605,567 B2
(45) Date of Patent: Apr. 21, 2026

(54) NEUTRON CAPTURE THERAPY APPARATUS

(71) Applicant: NEUBORON THERAPY SYSTEM LTD., Xiamen (CN)

(72) Inventors: Yuan-hao Liu, Xiamen (CN); Wei-lin Chen, Xiamen (CN)

(73) Assignee: NEUBORON THERAPY SYSTEM LTD., Xiamen (CN)

( * ) Notice: Subject to any disclaimer, the term of this patent is extended or adjusted under 35 U.S.C. 154(b) by 606 days.

(21) Appl. No.: 18/082,648

(22) Filed: Dec. 16, 2022

(65) Prior Publication Data

US 2023/0124008 A1     Apr. 20, 2023

Related U.S. Application Data

(63) Continuation of application No. PCT/CN2021/104145, filed on Jul. 2, 2021.

(30) Foreign Application Priority Data

| Jul. 3, 2020 | (CN) | .......................... | 202010631538.8 |
| Sep. 30, 2020 | (CN) | .......................... | 202011060387.1 |

(51) Int. Cl.
*A61N 5/10* (2006.01)

(52) U.S. Cl.
CPC ......... *A61N 5/1077* (2013.01); *A61N 5/1048* (2013.01); *A61N 5/1065* (2013.01); *A61N 5/1067* (2013.01); *A61N 5/1071* (2013.01); *A61N 2005/1074* (2013.01); *A61N 2005/109* (2013.01); *A61N 2005/1092* (2013.01); *A61N 2005/1095* (2013.01)

(58) Field of Classification Search
None
See application file for complete search history.

(56) References Cited

U.S. PATENT DOCUMENTS

| 5,392,319 | A | 2/1995 | Eggers |
| 5,704,890 | A | 1/1998 | Bliss et al. |
| 5,984,023 | A | 11/1999 | Sharma et al. |
| 6,614,038 | B1 | 9/2003 | Brand et al. |
| 10,537,750 | B2 | 1/2020 | Liu et al. |
| 2003/0026374 | A1 | 2/2003 | Ruddy et al. |
| 2003/0076915 | A1 | 4/2003 | Matsumiya |
| 2003/0155530 | A1 | 8/2003 | Adnani et al. |

(Continued)

FOREIGN PATENT DOCUMENTS

| CN | 102648023 | A | 8/2012 |
| CN | 103083820 | A | 5/2013 |

(Continued)

OTHER PUBLICATIONS

International Search Report of PCT/CN2021/104145, Jul. 2, 2021.

(Continued)

*Primary Examiner* — Eliza W Osenbaugh-Stewart
(74) *Attorney, Agent, or Firm* — Troutman Pepper Locke LLP; Tim Tingkang Xia, Esq.

(57) ABSTRACT

Disclosed is a neutron capture therapy apparatus. The neutron capture therapy apparatus is used for irradiating a neutron beam with a preset neutron dose to an object to be irradiated. The neutron beam enters the object and undergoes a nuclear reaction with boron in the object. The neutron capture therapy apparatus includes a correction system for correcting the preset neutron dose.

8 Claims, 5 Drawing Sheets

(56) References Cited

U.S. PATENT DOCUMENTS

| | | |
|---|---|---|
| 2007/0045546 A1 | 3/2007 | Hsi et al. |
| 2011/0101234 A1 | 5/2011 | Nakamura et al. |
| 2012/0027162 A1 | 2/2012 | Garnica Garza |
| 2016/0114357 A1 | 4/2016 | Dillon |
| 2016/0180977 A1 | 6/2016 | Ito et al. |
| 2017/0115428 A1 | 4/2017 | Zhou et al. |
| 2017/0329028 A1 | 11/2017 | Kunimoto |
| 2018/0250528 A1 | 9/2018 | Liu et al. |
| 2018/0326225 A1 | 11/2018 | Liu et al. |
| 2019/0099619 A1 | 4/2019 | Maltz |
| 2019/0209870 A1 | 7/2019 | Ueno et al. |
| 2019/0255362 A1 | 8/2019 | Voronenko et al. |
| 2019/0317229 A1 | 10/2019 | Radel et al. |
| 2020/0069974 A1 | 3/2020 | Piestrup et al. |
| 2020/0086029 A1 | 3/2020 | Marterstock |
| 2020/0114172 A1 | 4/2020 | Ueno et al. |
| 2020/0124743 A1 | 4/2020 | Usui et al. |

FOREIGN PATENT DOCUMENTS

| | | |
|---|---|---|
| CN | 104174121 A | 12/2014 |
| CN | 105120952 A | 12/2015 |
| CN | 105190361 A | 12/2015 |
| CN | 105938731 A | 9/2016 |
| CN | 106552321 A | 4/2017 |
| CN | 106552322 A | 4/2017 |
| CN | 106975162 A | 7/2017 |
| CN | 106980136 A | 7/2017 |
| CN | 108431635 A | 8/2018 |
| CN | 108744320 A | 11/2018 |
| CN | 108853751 A | 11/2018 |
| CN | 108905004 A | 11/2018 |
| CN | 109011203 A | 12/2018 |
| CN | 109011221 A | 12/2018 |
| CN | 109308733 A | 2/2019 |
| CN | 110418666 A | 11/2019 |
| EP | 2805745 A1 | 11/2014 |
| EP | 3321714 A1 | 5/2018 |
| JP | 1983027298 A | 2/1983 |
| JP | 2000024125 A | 1/2000 |
| JP | 2013183838 A | 9/2013 |
| JP | 2014145638 A | 8/2014 |
| JP | 2014228401 A | 12/2014 |
| JP | 2016159107 A | 9/2016 |
| JP | 2016214760 A | 12/2016 |
| JP | 2017009393 A | 1/2017 |
| JP | 2017058162 A | 3/2017 |
| JP | 6363497 B2 | 7/2018 |
| JP | 2019501737 A | 1/2019 |
| JP | 6565113 B2 | 8/2019 |
| JP | 2019152436 A | 9/2019 |
| JP | 2019194521 A | 11/2019 |
| RU | 79681 U1 | 1/2009 |
| RU | 2695296 C1 | 7/2019 |
| RU | 2697763 C1 | 8/2019 |
| TW | I520758 B | 2/2016 |
| TW | 201834715 A | 10/2018 |
| TW | I666037 B | 7/2019 |
| WO | 2005008287 A1 | 1/2005 |
| WO | 2012014671 A1 | 2/2012 |
| WO | 2013146690 A1 | 10/2013 |
| WO | 2014156245 A1 | 10/2014 |
| WO | 2017081768 A1 | 5/2017 |
| WO | 2017121337 A1 | 7/2017 |
| WO | 2018168713 A1 | 9/2018 |
| WO | 2018205403 A1 | 11/2018 |
| WO | 2020111085 A1 | 6/2020 |

OTHER PUBLICATIONS

Sung-Joon Ye et al., Boron self-shielding effects on dose delivery of neutron capture therapy using epithermal beam and boronophenylalanine, Med. Phys. 26 (11), 1999.

Jianguo Sun, Digital Intelligent Radiotherapy, Shandong Science and Technology Press, National Science and Technology Academic Works Publishing Fund Supported Publication, 2019, Editorial Team: Han Lin, Cui Lijun, Design: Sun Xiaojie.

NEUTRON CAPTURE THERAPY APPARATUS

CROSS-REFERENCE TO RELATED PATENT APPLICATION

This application is a continuation application of International Application No. PCT/CN2021/104145, filed on Jul. 2, 2021, which claims priority to Chinese Patent Application No. 202010631538.8, filed on Jul. 3, 2020, and Chinese Patent Application No. 202011060387.1, filed on Sep. 30, 2020, the disclosures of which are hereby incorporated by reference.

TECHNICAL FIELD

The disclosure relates to the field of radioactive ray irradiation, and in particular to a neutron capture therapy apparatus.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the disclosure.

With the development of atomics, radio therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy often has poor treatment effect on malignant tumors (for example, glioblastoma multiforme and melanoma) with radio resistance.

In order to reduce radiation injury to normal tissues around tumors, a target therapy concept in chemotherapy is applied to radiotherapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example, boron neutron capture therapy. By means of specific aggregation of boron-containing drugs in tumor cells and cooperating with precise neutron beam control, a cancer treatment choice better than traditional radioactive rays is provided.

During the boron neutron capture therapy, an irradiation dosage applied to a sick body needs to be controlled accurately due to stronger neutron beam radioactive rays performing radiotherapy on the sick body. However, when a therapy plan is formulated, there are still problems of inaccurate setting of preset irradiation parameters, such as a neutron irradiation dosage, and inaccurate detection of an actual irradiation dosage.

Furthermore, during an actual irradiation, an event that an instruction is input by mistake or relevant instructions and irradiation parameters are changed occurs occasionally, due to a fact that an operator or a doctor accidentally touches a control panel by mistake, so that a medical risk is increased.

SUMMARY

In order to solve the above problems, the disclosure provides a neutron capture therapy apparatus capable of applying an accurate neutron irradiation dosage to an object to be irradiated, and including a neutron beam irradiation system configured to generate a neutron beam, a detection system configured to detect irradiation parameters during a neutron beam irradiation therapy, and a correction system configured to correct a preset neutron dosage.

Further, the correction system may correct the preset neutron dosage according to a real-time boron concentration and a neutron flux in the object to be irradiated.

Further, the neutron capture therapy apparatus may further include a detection system, the detection system includes a neutron dosage detection device configured to detect a dosage of the neutron beam in real time and a boron concentration detection device configured to detect a boron concentration in the object to be irradiated.

Further, correction coefficients used by the correction system may include a boron self-shielding effect correction coefficient $K_s$ calculated by using a formula (3-6):

$$K_s = \frac{\varphi_B}{\varphi_{B0}} \tag{3-6}$$

where $\varphi_B$ is a thermal neutron flux in the object to be irradiated when a boron concentration distribution is B, and $\varphi_{B0}$ is a thermal neutron flux in the object to be irradiated when a boron concentration distribution is $B_0$.

Further, the correction coefficients may further include a positioning correction coefficient $K_p$, calculated by using a formula (3-2):

$$K_p = \frac{D}{D_0} \tag{3-2}$$

where D is a real-time neutron dosage measured by the neutron dosage detection device, and $D_0$ is an uncorrected preset neutron dosage.

Further, the uncorrected preset neutron dosage $D_0$ may be calculated by using a formula (3-7) as follows:

$$D_0 = D_B \cdot B_{con} \cdot CBE + D_f \cdot RBE_n + D_{th} \cdot RBE_n + D_r \cdot RBE_r \tag{3-7}$$

where $D_B$ is a dosage at the boron concentration of 1 ppm, $B_{con}$ is an actually measured boron concentration, $D_f$ is a fast neutron dosage, $D_{th}$ is a thermal neutron dosage, $RBE_n$ is a RBE of the neutron, $D_r$ is a gamma dosage, and $RBE_r$ is a gamma RBE.

Further, the correction coefficients may further include a neutron beam intensity correction coefficient $K_i$ calculated by using a formula (3-3):

$$K_i = \frac{I}{I_0} \tag{3-3}$$

where I is a real-time neutron dosage rate measured by the neutron dosage detection device, and $I_0$ is a theoretical beam intensity.

Further, the correction coefficients may further include a boron concentration correction coefficient $K_b$ calculated by using a formula (3-5):

$$K_b = \frac{B}{B_0} \tag{3-5}$$

where B is a real-time boron concentration detected by the boron concentration detection device, and $B_0$ is a boron concentration set value in a therapy plan.

Further, the correction coefficients may include a neutron correction coefficient $K_1$ and a boron correction coefficient $K_2$ calculated by using a formula (3-1) and a formula (3-4) respectively:

$$K_1 = K_p \cdot K_i \tag{3-1}$$

$$K_2 = K_b \cdot K_s \tag{3-4}$$

where $K_p$ is a positioning correction coefficient, $K_i$ is a neutron beam intensity correction coefficient, $K_b$ is a boron concentration correction coefficient, and $K_s$ is a boron self-shielding effect correction coefficient.

Further, a corrected preset neutron dosage $D_{total}$ may be calculated by using a formula (3-8) as follows:

$$D_{total} = K_1 \cdot (K_2 \cdot D_B \cdot B_{con} \cdot CBE + D_f \cdot RBE_n + D_{th} \cdot RBE_n + D_r \cdot RBE_r) \tag{3-8}$$

where $D_B$ is a dosage at the boron concentration of 1 ppm and has a unit Gy, $B_{con}$ is an actually measured boron concentration and has a unit ppm, $D_f$ is a fast neutron dosage and has a unit Gy, $D_{th}$ is a thermal neutron dosage and has a unit Gy, $RBE_n$ is a RBE of the neutron, $D_r$ is a gamma dosage and has a unit Gy, and $RBE_r$ is a gamma RBE.

Further, a first boron concentration value in the object to be irradiated is obtained by the boron concentration detection device, and a first boron self-shielding effect correction coefficient is obtained by the correction system; a second boron concentration value in the object to be irradiated is obtained by the boron concentration detection device, and a second boron self-shielding effect correction coefficient is obtained by the correction system, here the first boron concentration value is greater than the second boron concentration value, and the first boron self-shielding effect correction coefficient is less than the second boron self-shielding effect correction coefficient.

The neutron capture therapy apparatus of the disclosure is provided with a correction system configured to correct the preset neutron dosage, so that accuracy of the dosage of the neutron beam irradiated to the object to be irradiated is ensured from the source.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

In order to make purposes, technical solutions and technical effects of the disclosure clearer and enable those skilled in the art to implement them accordingly, the disclosure will be further described in detail below in combination with the accompanying drawings and embodiments.

In the following descriptions, terms "first", "second", or the like, may be used here to describe various elements, but these elements are not limited by these terms, and these terms are used to distinguish the described objects without any order or technical meaning.

Radiotherapy is a common means for treating cancers, and Boron Neutron Capture Therapy (BNCT) is an effective means for treating cancers and has been used increasingly in recent years. As shown in FIG. 1 to FIG. 7, a neutron capture therapy device irradiating a neutron beam of a preset neutron dosage an object to be irradiated, such as a sick body S, so as to perform BNCT includes a neutron beam irradiation system 1, a detection system, a monitoring system 3, a correction system and an anti-misoperation system. The neutron beam irradiation system 1 is configured to generate a neutron beam suitable for performing the neutron irradiation therapy on the sick body S. The detection system is configured to detect irradiation parameters such as a neutron dosage, or the like, during the neutron irradiation therapy. The monitoring system 3 is configured to control the whole neutron beam irradiation process. The correction system is configured to correct a preset neutron dosage. The anti-misoperation system is configured to prevent related personnel from inputting wrong instructions and information to the monitoring system 3.

BNCT produces two heavily charged particles 4He and 7Li by using a characteristic of a boron-containing (10B) drug having a high capture section for a thermal neutron, and through $10B(n,\alpha)7Li$ neutron capture and a nuclear fission reaction. The two heavily charged particles each has an average energy of about 2.33 MeV, and has characteristics of high Linear Energy Transfer (LET) and a short range. The LET and range of the 4He particle are 150 keV/μm and 8 μm respectively, the LET and range of the 7Li heavily charged particle are 175 keV/μm and 5 μm respectively, and a total range of the two heavily charged particles is approximately equivalent to a size of a cell, so that radiation damage to an organism may be limited to the cell level. The boron-containing drug is selectively gathered in tumor cells. After the neutron beam enters a body of the sick body S, it undergoes a nuclear reaction with boron in the body of the sick body S, to produce two heavily charged particles $^4$He and $^7$Li, and the two heavily charged particles $^4$He and $^7$Li locally kill the tumor cells without causing too much damage to normal tissues.

Figure 1:
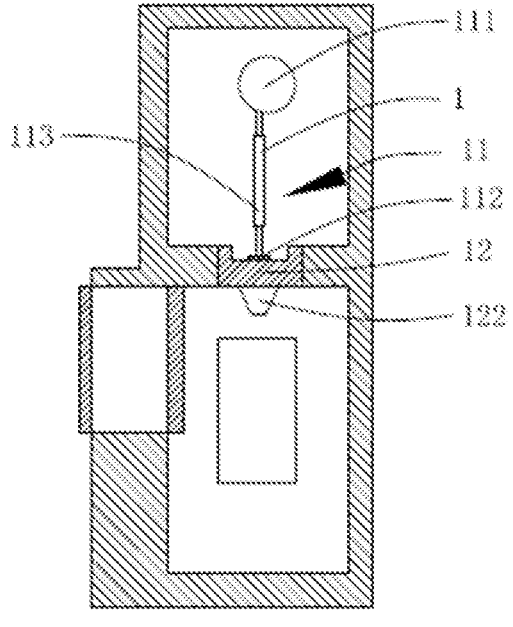
FIG. 1 is a schematic diagram of a neutron beam irradiation system of a neutron capture therapy device of the disclosure.

As shown in FIG. 1, the neutron beam irradiation system 1 includes a neutron beam generation module 11 and a beam adjustment module 12 configured to adjust a neutron beam generated by the neutron beam generation module 11.

The neutron beam generation module 11 generates the neutron beam irradiated to the sick body S, and includes an accelerator 111 configured to accelerate a charged particle beam, a target 112 configured to react with the charged particle beam to generate the neutron beam, and a charged particle beam transport part 113 located between the accelerator 111 and the target 112 and configured to transport the charged particle beam. The charged particle beam transport part 113 transports the charged particle beam to the target 112, and has one end connected to the accelerator 111 and the other end connected to the target 112. Furthermore, the charged particle beam transport part 113 is provided with a beam control device, such as a beam adjustment part (not shown), a charged particle scanning part (not shown), or the like. The beam adjustment part controls a travelling direction and a beam diameter of the charged particle beam. The charged particle beam scanning part scans the charged particle beam and controls an irradiation position of the charged particle beam relative to the target 112.

The accelerator 111 may be a cyclotron, a synchrotron, a synchrocyclotron, a linear accelerator, or the like. The commonly used target 112 includes lithium (Li) target and beryllium (Be) target. The charged particle beam is accelerated to an energy sufficient to overcome Coulomb repulsion of nuclei of the target 112 and undergoes a $^7Li(p, n)^7Be$ nuclear reaction with the target 112 to generate the neutron beam. The commonly discussed nuclear reaction includes $^7Li(p, n)^7Be$ and $^9Be(p, n)^9B$. Usually, the target 112 includes a target layer and an anti-oxidation layer located on a side of the target layer and configured to prevent oxidation of the target layer, and the anti-oxidation layer is made of Al or stainless steel.

In the embodiments disclosed in the disclosure, the accelerator 111 accelerates charged particles to allow them to undergo a nuclear reaction with the target 112 to supply a neutron source. In other embodiments, the neutron source may be supplied by using a nuclear reactor, a D-T neutron generator, a D-D neutron generator, or the like. However, no matter whether the neutron source is supplied by accelerating the charged particles to allow them to undergo the nuclear reaction with the target 112, as disclosed in the disclosure, or the neutron source is supplied by the nuclear reactor, the D-T neutron generator, the D-D neutron generator, or the like, a mixed irradiation field is generated, that is, the generated beam includes a high-speed neutron beam, an epithermal neutron beam, a thermal neutron beam and a gamma ray. During BNCT, the higher the content of the rest of irradiation rays (collectively referred to as irradiation ray contamination) except for the epithermal neutron, the greater the proportion of non-selective dosage deposition in normal tissues, therefore radiation causing unnecessary dosage deposition may be reduced.

The International Atomic Energy Agency (IAEA) has given five air beam quality factor recommendations for the neutron source used by clinical BNCT. The five recommendations may compare advantages and disadvantages of different neutron sources, and serve as a reference for selecting a neutron generation pathway and designing a beam shaping body 121. The five recommendations are as follows:

Epithermal neutron flux$>1\times10^9$ n/cm$^2$s

Fast neutron contamination $<2\times10^{-13}$ Gy-cm$^2$/n

Photon contamination $<2\times10^{-13}$ Gy-cm$^2$/n

Thermal to epithermal neutron flux ratio $<0.05$

Epithermal neutron current to flux ratio $>0.7$

Note: an epithermal neutron has an energy region between 0.5 eV and 40 keV, a thermal neutron has an energy region less than 0.5 eV, and a fast neutron has an energy region greater than 40 keV.

Figure 2:
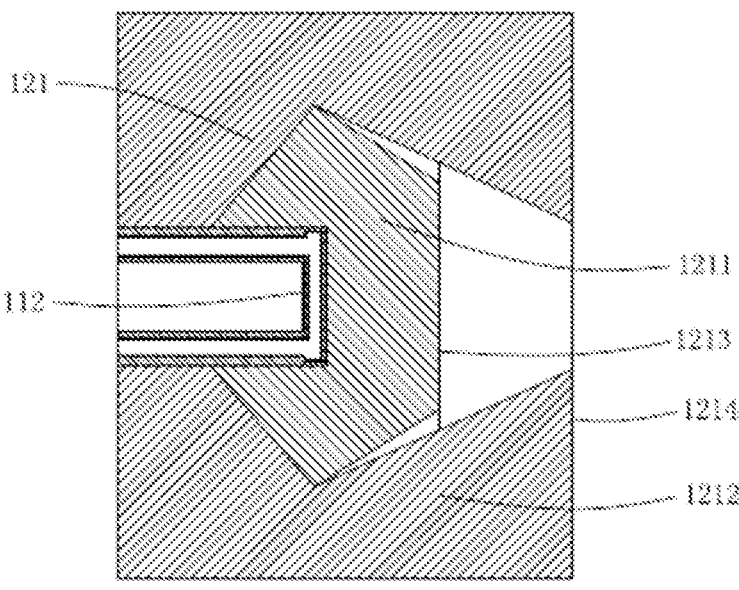
FIG. 2 is a schematic diagram of a beam shaping body of a neutron capture therapy device of the disclosure.
Figure 3:
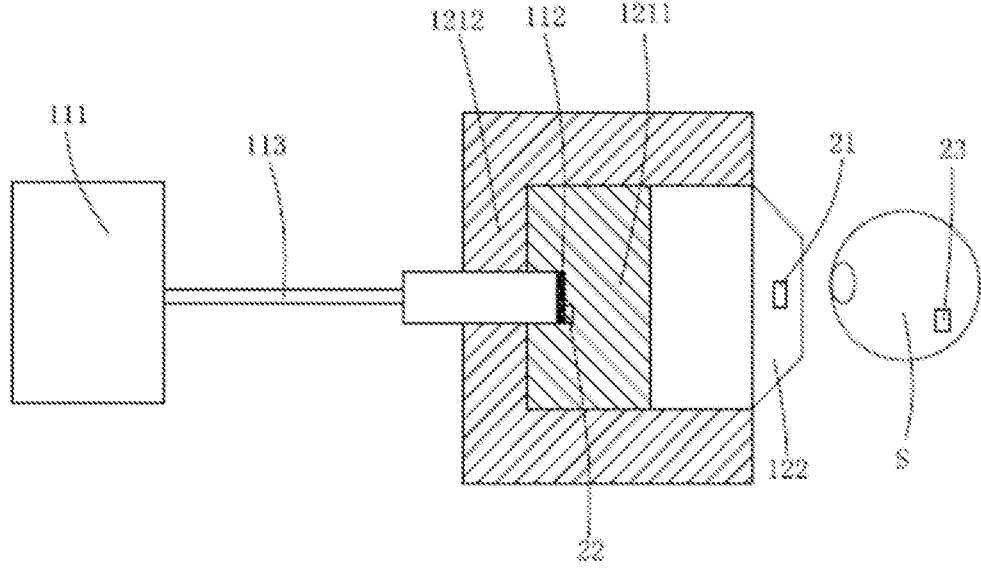
FIG. 3 is a schematic diagram of a neutron beam irradiation system and a detection system of a neutron capture therapy device of the disclosure.

As shown in combination with FIG. 2 and FIG. 3, the beam adjustment module 12 is configured to adjust mixed irradiation rays generated in the neutron beam generation module 11, so as to reduce the irradiation ray contamination irradiated to the sick body S and focus an epithermal neutron for treating the sick body S to a part, needed to be irradiated, of the sick body S. The beam adjustment module 12 includes the beam shaping body 121 configured to decelerate and shield the neutron beam, and a collimator 122 configured to focus the epithermal neutron to the part, needed to be irradiated, of the sick body S. The beam shaping body 121 includes a retarder 1211 configured to decelerate the neutron beam generated from the target 112 to an energy region of the epithermal neutron, a reflector 1212 configured to guide a deviated neutron back to the retarder 1211 to increase a beam intensity of the epithermal neutron, a thermal neutron absorber 1213 configured to absorb a thermal neutron to avoid excessive dosage deposition in superficial normal tissues during therapy, and a radiation shield 1214 configured to shield a leaked neutron and photon to reduce dosage deposition in normal tissues at a non-irradiated region. In other embodiments, the thermal neutron absorber may not be included, instead the thermal neutron is absorbed by substances contained in the retarder or the reflector, or it may be understood that the retarder and the thermal neutron absorber are integrally provided. In other embodiments, the radiation shield may not be included, instead the radiation shield may be made of the same material as the reflector, or it may be understood that the reflector and the radiation shield are integrally provided.

The retarder 1211 may be formed by stacking multiple different materials. The material of the retarder 1211 is selected according to factors, such as energy of the charged particle beam, or the like. For example, when energy of a proton beam from the accelerator 111 is 30 MeV and the Be target is used, the material of the retarder 1211 is lead (Pb), iron, aluminum (Al) or calcium fluoride. When the energy of the proton beam from the accelerator 111 is 11 MeV and the Be target is used, the material of the retarder 1211 is heavy water ($D_2O$), or lead fluoride, or the like. As an embodiment, the retarder 1211 is formed by mixing $MgF_2$ and LiF which is 4.6% of $MgF_2$ by weight percentage, the reflector 1212 is made of Pb, and the thermal neutron absorber 1213 is made of $^6Li$. The radiation shield 1214 includes a photon shield and a neutron shield. Here the photon shield is made of Pb and the neutron shield is made of polyethylene (PE). The retarder 1211 may be formed in a bi-conical shape as disclosed in FIG. 2 or a cylindrical shape as disclosed in FIG. 3. The reflector 1212 is arranged around the retarder 1211, and has a shape adaptively changed according to the shape of the retarder 1211.

Continuing to refer to FIG. 3, the detection system includes a neutron dosage detection device 21 configured to detect the neutron dosage of the neutron beam in real time, a temperature detection device 22 configured to detect temperature of the target 112, a displacement detection device 23 configured to detect whether the sick body S generates displacement during therapy, and a boron concentration detection device (not shown) configured to detect the boron concentration in the body of the sick body S.

Figure 4:
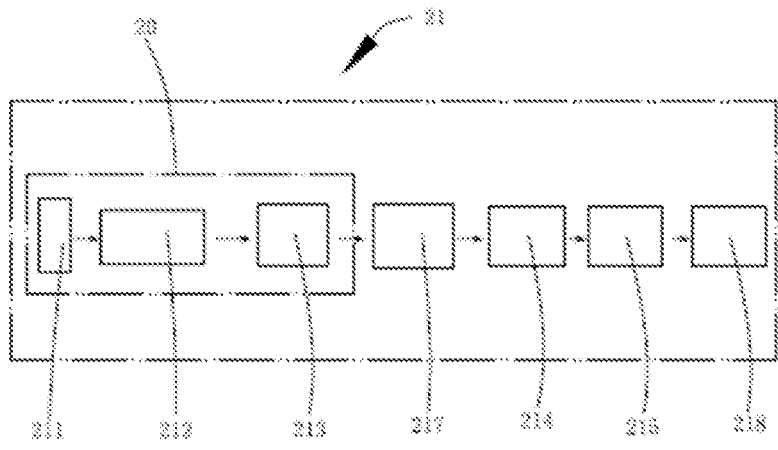
FIG. 4 is a schematic diagram of a neutron dosage detection device in a first embodiment of a neutron capture therapy device of the disclosure.
Figure 5:
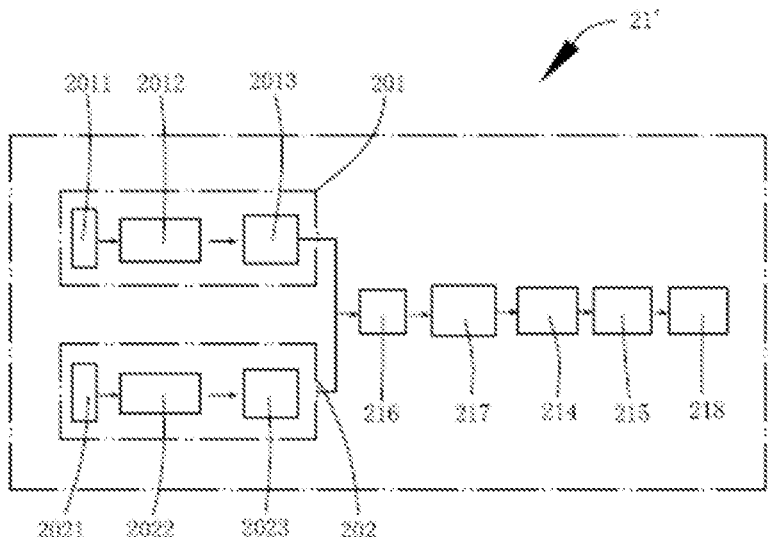
FIG. 5 is a schematic diagram of a neutron dosage detection device in a second embodiment of a neutron capture therapy device of the disclosure.

As shown in combination with FIG. 4, the neutron dosage detection device 21 includes a detector 211 configured to receive the neutron and output a signal, a signal processing unit 212 configured to process the signal output from the detector 211, a counter 213 configured to count a signal output from the signal processing unit 212 to obtain a counting rate, a conversion unit 214 configured to convert the counting rate recorded by the counter 213 into a neutron flux rate or a neutron dosage rate, an integration unit 215 configured to integrate the neutron flux rate or the neutron dosage rate to obtain the neutron dosage, and a display 218 configured to display the neutron dosage. The detector 211, the signal processing unit 212 and the counter 213 form a counting rate channel 20.

The detector 211 may be placed in the beam shaping body 121, may also be placed in the collimator 122, or may also be arranged at any position adjacent to the beam shaping body 121, as long as the position where the detector 211 is located may be configured to detect the neutron dosage of the neutron beam.

The detector 211 capable of detecting the neutron dosage of the neutron beam in real time is provided with an ionization chamber and a scintillation detector. Here a He-3 proportional counter, a $BF_3$ proportional counter, a fission chamber, and a boron ionization chamber use a structure of the ionization chamber as a substrate, and the scintillator detector contains an organic material or an inorganic material. When the thermal neutron is detected, the scintillator detector usually adds a high thermal neutron capture section element such as Li, or B, or the like. A certain element in two types of detectors captures the neutron entering the detector or undergoes the nuclear fission reaction with the neutron entering the detector to release heavily charged particles and nuclear fission fragments, which generate a large number of ionization pairs in the ionization chamber or the scintillation detector, and these charges are collected and form an electrical signal. The signal processing unit 212 performs noise reduction, conversion and separation processing on the electrical signal, and the electrical signal is converted into a pulse signal. A neutron pulse signal and a γ pulse signal are distinguished by analyzing a magnitude of a voltage pulse. The separated neutron pulse signal is continuously recorded by the counter 213 to obtain the counting rate (n/s) of the neutron. The conversion unit 214 calculates and converts the counting rate through internal software, programs, or the like, to obtain the neutron flux rate ($cm^{-2}s^{-1}$), and further calculates and converts the neutron flux rate to obtain the neutron dosage rate (Gy/s). And the integration part integrates the neutron dosage rate to obtain the real-time neutron dosage.

A brief introduction is made below by example of the fission chamber, the scintillator detector and the $BF_3$ detector.

When the neutron beam passes through the fission chamber, it dissociates with gas molecules inside the fission chamber or a wall of the fission chamber to generate an electron and a positively charged ion, which are referred to as the ion pair as described above. Due to a high voltage of an electric field applied in the fission chamber, the electron moves towards a central anode wire and the positively charged ion moves towards a surrounding cathode wall, so that a measurable electrical signal is generated.

Substances, such as an optical fiber, or the like, in the scintillation detector absorb energy and generate visible light, which uses ionizing radiation to excite an electron in a crystal or molecule to an excited state. Fluorescence emitted when the electron returns to a ground state is collected and serves as detection of the neutron beam. The visible light emitted by action of the scintillation detector and the neutron beam is converted into an electrical signal by using a photomultiplier tube, to be output.

The $BF_3$ detector is placed in the beam shaping body 121 and configured to receive irradiation of the neutron beam, an element B in the $BF_3$ detector undergoes a nuclear reaction $^{10}B(n, alpha)^7Li$ with the neutron, and alpha particles generated by the nuclear reaction and $^7Li$ electric particles are collected by a high voltage electrode under driving of the voltage, to generate an electrical signal. The electrical signal is transmitted to the signal processing unit 212 through a coaxial cable, to be subject to signal amplification, filtering and shaping, so as to form a pulse signal. The processed pulse signal is transmitted to the counter 213, to count pulses therein, so as to obtain the counting rate (n/s) through which intensity of the neutron beam, i.e., the neutron dosage, may be measured in real time.

The temperature detection device 22 is a thermocouple, and two conductors with different components (referred to as thermocouple wires or hot electrodes) are connected at both ends to form a loop. When temperature of the connection point is different, an electromotive force may be generated in the loop. This phenomenon is referred to as a thermoelectric effect, and the electromotive force is referred to as thermoelectric potential. The thermocouple performs temperature measurement by using this principle, of which one end directly configured to measure temperature of a medium is referred to as a working end (also known as a measurement end), and the other end is referred to as a cold end (also known as a compensation end). The cold end is connected to a display instrument or an assorted instrument, and the display instrument may indicate the thermoelectric potential generated by the thermocouple. Of course, as known by those skilled in the art, the temperature detection device 22 may also be any detector 211 capable of detecting temperature, such as a resistance thermometer, or the like.

The displacement detection device 23 is an infrared signal detector, and the infrared detector operates by detecting infrared rays emitted by a human body. The infrared detector collects infrared radiation from the outside and gathers the infrared radiation on an infrared sensor. The infrared sensor usually uses a pyroelectric element, which releases charges to the outside when temperature of the infrared radiation changes, and an alarm is generated after detecting and processing charges. The detector 211 is aimed to detecting radiation of the human body. Therefore, a radiation-sensitive element is very sensitive to infrared radiation with a wavelength of about 10 μm. Of course, it is well known by those skilled in the art that the displacement detection device 23 may be any detection device suitable for detecting change of displacement of an object to be irradiated, such as a displacement sensor. The displacement sensor determines whether the object to be irradiated moves, according to the change of displacement of the object to be irradiated relative to a certain reference object. It is also well known by those skilled in the art that the displacement detection device 23 not only may be configured to detect the change of displacement of the object to be irradiated, but also may be configured to detect change of displacement of a support member and/or a treatment table fixing the object to be irradiated, thereby indirectly knowing the change of displacement of the object to be irradiated.

During the neutron beam irradiation therapy for the sick body S, boron is continuously supplied to the sick body S as needed. A boron concentration may be detected by an inductively coupled plasma spectroscopy, a high-resolution α autoradiography, a charged ion spectroscopy, a neutron capture camera, a nuclear magnetic resonance imaging and a magnetic resonance imaging, a positive electron emission tomography, a prompt γ-ray spectroscopy, or the like, and a device involved in the above detection method is referred to as a boron concentration detection device.

The disclosure is described by example of calculating the boron concentration in the body of the sick body S by detecting γ-ray released by the sick body S. The neutron beam enters the body of the sick body and reacts with boron to generate γ-ray. By measuring the amount of γ-ray, the amount of boron reacting with the neutron beam may be calculated, thereby calculating the boron concentration in the body of the sick body S. The boron concentration detection device is configured to measure the boron concentration in the body of the sick body S in real time when the neutron beam irradiation system 1 performs the neutron beam irradiation therapy on the sick body S.

The boron concentration detection device detects γ-ray (478 keV) generated by reaction between the neutron and boron, to measure the boron concentration, and a boron distribution measurement system (PG(Prompt-γ)-SPECT) capable of measuring a single-energy γ-ray to measure distribution of the boron concentration is used as the boron concentration detection device. The boron concentration detection device includes a γ-ray detection part and a boron concentration calculation part. The γ-ray detection part detects information related to γ-ray emitted from the body of the sick body S, and the boron concentration calculation part calculates the boron concentration in the body of the sick body S according to the information related to γ-ray detected by the γ-ray detection part. The γ-ray detection part may use the scintillator and various other γ-ray detection devices. In the implementation, the γ-ray detection part is arranged in the vicinity of a tumor of the sick body S, for example, at a position about 30 cm away from the tumor of the sick body S.

The detector 211 of the above neutron dosage detection device 21 configured to detect the neutron dosage of the neutron beam belongs to a pulse detector, and a shortest time interval between two consecutively incident neutrons distinguished by the detector 211 is described as a pulse resolution time τ(s). The detector 211 may not record other incident neutrons accurately within i time after a neutron is incident on the detector 211, thus it is also referred to as dead time.

Sensitivity of the detector 211 detecting the neutron is a ratio of total output of the detector 211 to a corresponding total input. For the detector 211 of the neutron dosage detection device 21 exemplified in the disclosure, the input physical quantity of the detector is the neutron beam, and its output physical quantity is usually an optical signal or an electrical signal. The higher the ratio of the total output to the corresponding total input, the higher the sensitivity of the detector 211 detecting the neutron. The higher the sensitivity of detecting the neutron, the shorter the pulse resolution time τ corresponding to the detector 211. Usually, in order to reduce a statistical error, the detector 211 with high sensitivity of detecting the neutron detects a low-flux beam, and the detector 211 with low sensitivity of detecting the neutron detects a high-flux beam.

Different embodiments are described in detail below. For simplicity, the same component has the same digital identifier in different embodiments, and similar components are distinguished by the same digital identifier plus "'" or "''" in different embodiments.

In the first embodiment disclosed in FIG. 4, the neutron dosage detection device 21 is provided with a counting rate channel 20. In order to accurately detect neutron dosages of neutron beams of different fluxes, in the second embodiment disclosed in FIG. 5, the neutron dosage detection device 21' includes at least two counting rate channels 20'. The detector 211' of each counting rate channel 20' has a different sensitivity of detecting the neutron. Further, the neutron dosage detection device 21' further includes a counting rate channel selection unit 216 configured to select an appropriate counting rate channel 20' according to a current power of the accelerator 111 or a neutron beam flux. In the second embodiment, the neutron dosage detection device 21' includes at least two counting rate channels 20', a counting rate channel selection unit 216 configured to select an appropriate counting rate channel 20' from the at least two counting rate channels 20', a conversion unit 214 configured to convert a counting rate recorded by the counting rate channel 20' selected by the counting rate channel selection unit 216 into the neutron flux rate or the neutron dosage rate, and an integration unit 215 configured to integrate the neutron flux rate or the neutron dosage rate to obtain the neutron dosage.

The two counting rate channels 20' are named as a first counting rate channel 201 and a second counting rate channel 202 respectively. The first counting rate channel 201 includes a first detector 2011 configured to receive the neutron and output a signal, a first signal processing unit 2012 configured to process the signal output from the first detector 2011, and a first counter 2013 configured to count a signal output from the first signal processing unit 2012. The second counting rate channel 202 includes a second detector 2021 configured to receive the neutron and output a signal, a second signal processing unit 2022 configured to process the signal output from the second detector 2021, and a second counter 2023 configured to count a signal output from the second signal processing unit 2022. The counting rate channel selection unit 216 selects an appropriate counting rate channel 20 according to a current power of the accelerator 111 or a neutron beam flux. The conversion unit 214 converts a counting rate recorded by the counting rate channel 20 selected by the counting rate channel selection unit 216 into the neutron flux rate or the neutron dosage rate. The integration unit 215 integrates the neutron flux rate or the neutron dosage rate to obtain the neutron dosage.

Usually, a neutron flux which may be generated when the accelerator 111 is at a maximum power is described as a maximum neutron flux. When a detected real-time neutron flux is less than half of the maximum neutron flux, it is considered as a small neutron flux. When the detected real-time neutron flux is greater than or equal to half of the maximum neutron flux, it is considered as a large neutron flux.

Sensitivity of the first detector 2011 detecting the neutron is a first sensitivity, sensitivity of the second detector 2021 detecting the neutron is a second sensitivity, and the first sensitivity is less than the second sensitivity. The first detector 2011 is wrapped with a large number of neutron absorbing materials, such as $B_4C$, Cd, or is filled with a low-pressure working gas, or is designed to be small in size, thereby reducing the sensitivity of detecting the neutron. When the neutron flux is large, the first detector 2011 is used for detection, so that a counting rate loss caused by the pulse resolution time may be reduced. Compared with the first detector 2011, the second detector 2021 is wrapped with a small number of neutron absorbing materials, or is not wrapped with any material, or is filled with a high-pressure working gas, or is designed to be large in size, so that the second sensitivity is greater than the first sensitivity. When the neutron flux is small, the second detector 2021 is used for detection, so that a statistical error of a counting rate caused by a low counting rate may be reduced.

Correspondingly, the sensitivity of the first counting rate channel 201 detecting the neutron is smaller than the sensitivity of the second counting rate channel 202 detecting the neutron. A counting rate selection unit selects an appropriate counting rate channel 20' according to a current power of the accelerator 111 or a neutron flux. For example, in the case where a maximum beam intensity of the accelerator 111 is 10 mA, when a beam intensity of the accelerator 111 is greater than 5 mA, a counting rate recorded by the first counter 2013 of the first counting rate channel 201 with the first sensitivity is selected to be transmitted to the conversion unit 214 for dosage calculation; and when a beam intensity of the accelerator 111 is less than 5 mA, a counting rate recorded by the second counter 2023 of the second counting rate channel 202 with the second sensitivity is selected to be transmitted to the conversion unit 214 for dosage calculation. A more accurate counting rate is selected by the counting rate selection unit to be transmitted to the conversion unit 214 for dosage calculation, thereby obtaining an accurate neutron irradiation dosage.

The neutron dosage detection device 21 is provided with at least two counting rate channels with different sensitivities of detecting the neutron, i.e., the first counting rate channel 201 and the second counting rate channel 202, and the counting rate channel selection unit 216 selects a more accurate counting rate according to an actual situation, to calculate the neutron dosage, so that a counting rate loss error caused by the pulse resolution time may be reduced. At the same time, a statistical error caused by a low counting rate is considered, so that accuracy of real-time neutron dosage detection is improved, thereby improving accuracy of the neutron dosage of the neutron beam irradiated to the sick body S.

In other implementations, the counting rate channels 20 and 20' may be configured to be any number of counting rate channels, as needed.

Furthermore, in the implementations as exemplified above, the counting rate channel 20 is selected according to power of the accelerator 111, the neutron flux, or the like. In other implementations, the counting rate channel 20' may be selected according to a distance between the detector 211 and the neutron source. For example, when the detector 211 is arranged at a position close to the neutron source, the second counting rate channel 202 with the second sensitivity is selected; and when the detector 211 is arranged at a position away from the neutron source, the first counting rate channel 201 with the first sensitivity is selected.

The detector 211 of the above neutron dosage detection device 21 belongs to a pulse detector. Usually, the pulse detector has a problem of resolution of time. An incident neutron reacts with the detector 211 to generate a signal pulse, which may be followed by a time interval of $\tau$. Other signal pulses generated within the time interval may be considered as the same signal pulse by the detector 211. In this case, as long as a time interval between any two signal pulses is less than $\tau$, the second pulse may not be recorded. Therefore, the counting rate recorded by the counter 213 has a deviation and is needed to be corrected. The conversion unit 214 obtains a real-time accurate neutron flux rate and neutron dosage rate $D_t$ (Gy/s) according to the corrected counting rate $C_k$ in combination with the dosage conversion factor.

As shown in combination with FIG. 4 and FIG. 5 again, further, the neutron dosage detection device 21 further includes a counting rate correction unit 217 configured to correct the counting rate. The counting rate correction unit 217 includes a counting rate correction calculation part, a counting rate correction factor calculation part, and a pulse resolution time calculation part.

The counting rate correction calculation part calculates the corrected counting rate $C_k$ by using a formula (1-1):

$$C_k = K \cdot C_t \qquad (1\text{-}1)$$

where K is a counting rate correction factor; and
$C_t$ is a real-time counting rate recorded by the counter 213.

The counting rate correction factor calculation part calculates the counting rate correction factor K by using a formula (1-2):

$$K = \frac{n}{m} \qquad (1\text{-}2)$$

where n is the number of pulses recorded by the counter 213 in unit time, that is, the real-time counting rate (n/s) in unit time; and
m is the number of signal pulses actually generated within the detector 211 in unit time, that is, the number of neutrons (n/s) reacting with the detector 211 in unit time.

When the number of neutrons entering the detector 211 to react in unit time is m, and the number of pulses actually recorded by the counter 213 in unit time is n, the time when a counter tube may not operate is in, and the total number of neutrons which enter the counter tube at this time and may not be recorded is $mn\tau$, that is, the lost count is m−n, and a formula (1-3) is obtained by derivation:

$$n - m = nm\tau \qquad (1\text{-}3)$$

The formula (1-3) is substituted into the formula (1-2) to obtain a formula (1-4):

$$K = \frac{1}{1 - m\tau}(14) \qquad (1\text{-}4)$$

It may be known from the above formula that when the pulse resolution time is known, the counting rate correction factor may be calculated by combination of the number of pulses recorded by the counter 213 and the formula (1-4), and the counting rate correction factor may be substituted into the formula (1-1) to calculate the corrected counting rate.

Conventional pulse resolution time calculation methods include a double source method and a reactor power method. The two methods need two natural neutron sources or reactors to calculate, and have relatively high cost. Embodiments of the disclosure calculate the pulse resolution time based on the monitoring system of the neutron capture therapy device, which makes full use of existing devices and resources to reduce cost.

Firstly, the accelerator 111 is operated in a low flux state, and at this time, the neutron beam flux is a first neutron beam flux $I_1$, and the counting rate recorded by the counter 213 is $C_1$. Theoretically, due to the low flux state, the detector 211 is not affected by the pulse resolution time and there are signal pulses which may not be recorded. The accelerator 111 is operated to a high flux state, and at this time, the neutron beam flux is a second neutron beam flux $I_2$, and the counting rate recorded by the counter 213 is $C_2$. At this time, the counting rate is affected by the pulse resolution time, so that a part of signal pulses are not recorded, and the pulse resolution time calculation part calculates the pulse resolution time τ by using a formula (1-5):

$$\tau = \frac{\frac{I_2}{I_1} \cdot C_1 - C_2}{\frac{I_2}{I_1} \cdot C_1 \cdot C_2} \tag{1-5}$$

When position of the detector 211 does not change, the pulse resolution time does is not needed to be calculated during operation of the device every time. However, after the detector 211 operates for a long time, performance parameters of the detector 211 may change, to cause change of the pulse resolution time, therefore the pulse resolution time is needed to be calculated periodically.

The counting rate correction part 217 may calculate the pulse resolution time of the detector 211, and may calculate the counting rate correction factor according to the pulse resolution time, so that a counting rate error caused by the pulse resolution time is corrected, accuracy of real-time neutron dosage detection is further improved, and accuracy of the neutron dosage of the neutron beam irradiated to the sick body S is further improved.

Before irradiation therapy, the total neutron dosage to be delivered to the sick body S, the neutron flux rate or neutron dosage rate or current during irradiation, and the needed irradiation time, the irradiation angle and other irradiation parameters during irradiation are obtained by simulation, calculation, or the like. For convenience of description, the above parameters are collectively referred to as preset irradiation parameters. In other embodiments, a part of or more unmentioned parameters including the above parameters may be understood as the preset irradiation parameters, referred to as a preset neutron dosage (Gy), a preset neutron flux rate ($cm^{-2}s^{-1}$), a preset neutron dosage rate (Gy s$^{-1}$), a preset current (A), a preset irradiation time (s), or the like, respectively. During irradiation, due to change of some factors, the irradiation parameters are needed to be adjusted periodically according to relevant parameters detected by the detection system. The irradiation parameter detected by the detection system is named as the real-time irradiation parameter, and the adjusted irradiation parameter is named as the corrected irradiation parameter. The adjusted irradiation parameter may be the preset irradiation parameter or the corrected irradiation parameter.

Figure 6:
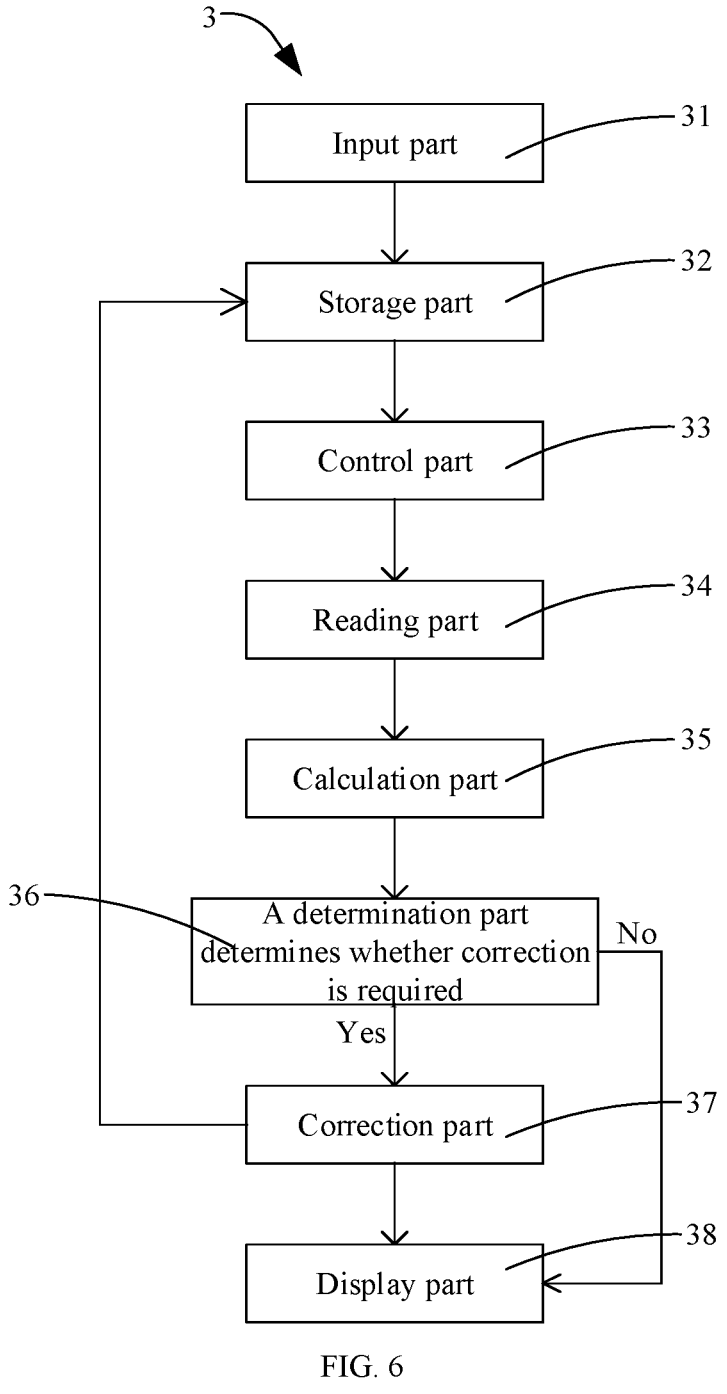
FIG. 6 is a schematic diagram of a monitoring system of a neutron capture therapy device of the disclosure.

As shown with reference to FIG. 6, the monitoring system 3 includes an input part 31 configured to input the preset irradiation parameters, a storage part 32 configured to store the irradiation parameters, a control part 33 configured to perform a therapy plan according to the irradiation parameters stored in the storage part 32, a reading part 34 configured to read the real-time irradiation parameters detected by the detection system, a calculation part 35 configured to calculate the real-time irradiation parameters and the preset irradiation parameters/the corrected irradiation parameters stored in the storage part 32, a determination part 36 configured to determine, according to a calculation result of the calculation part 35, whether the irradiation parameters are needed to be corrected, a correction part 37 configured to correct a part of the irradiation parameters stored in the storage part 32 when the determination part 36 determines that the irradiation parameters are needed to be corrected, and a display part 38 configured to display the remaining irradiation time or the remaining irradiation time and other irradiation parameters in real time.

Before the preset irradiation parameters are corrected, the irradiation parameters stored in the storage part 32 are the preset irradiation parameters, the irradiation parameters corrected by the correction part 37 are also the preset irradiation parameters, the remaining irradiation time displayed by the display part 38 is a difference value between the preset irradiation time and a real-time irradiation time, and the irradiation time displayed by the display part 38 is the preset irradiation time. After the preset irradiation parameters are corrected, the irradiation parameters stored in the storage part 32 are the corrected irradiation parameters, the irradiation parameters corrected by the correction part 37 again are also the corrected irradiation parameters, the remaining irradiation time displayed by the display part 38 is the corrected remaining irradiation time, and the irradiation parameters displayed by the display part 38 are the corrected irradiation parameters. Of course, the preset irradiation parameters and the corrected irradiation parameters may also be displayed at the same time.

In other embodiments, the input part 31, the storage part 32, or the like, may not be included.

The monitoring system 3 is electrically connected to the detection system, so that relevant information detected by the detection system may be transmitted to the monitoring system 3. The display 218 of the neutron dosage detection device 21 in the detection system and the display part 38 of the monitoring system 3 may be the same device, usually a display screen.

Operation process of the monitoring system 3 is shown with reference to FIG. 6, and descriptions thereof are as follows.

At S1, the preset irradiation parameters, such as a preset neutron flux rate or a preset neutron dosage rate or a preset current, a preset neutron dosage, a preset irradiation time, a preset boron concentration and other irradiation parameters, are input by the input part 31.

At S2, the irradiation parameters are stored by the storage part 32.

At S3, the therapy plan is performed by the control part 33 according to the irradiation parameters stored in the storage part 32.

At S4, the real-time irradiation parameters detected by the detection system are read by the reading part 34.

At S5, the irradiation parameters stored in the storage part 32 and the real-time irradiation parameters read by the reading part 34 are calculated by the calculation part 35.

At S6, whether the irradiation parameters stored in the storage part are needed to be corrected, is determined by the determination part 36 according to a calculation result of the calculation part 35.

At S7, latest irradiation parameters in the storage part 32 are corrected by the correction part 37, in response to the determination part 36 determining that the irradiation parameters stored in the storage part 32 are needed to be corrected; and a correction action is not performed by the correction part 37, in response to the determination part 36 determining that the irradiation parameters stored in the storage part 32 are not needed to be corrected.

At S8, the remaining irradiation time or are the remaining irradiation time and other irradiation parameters displayed by the display part 38 in real time, according to the irradiation parameters stored in the storage part 32.

During operation of the monitoring system 3, the reading part 34 periodically reads the real-time irradiation parameters, for example, read the real-time irradiation parameters every 5 minutes and transmits the real-time irradiation parameters to the calculation part 35 for related calculation. In response to the difference value between the real-time irradiation parameter and the preset irradiation parameter calculated by the calculation part 35 being greater than a first threshold, or in response to the real-time irradiation parameter being greater than a second threshold or less than a third threshold, the determination part 36 gives an instruction that the irradiation parameters are needed to be corrected. The correction part 37 corrects the irradiation parameters stored in the storage part 32. On the contrary, the determination part 36 gives an instruction that the irradiation parameters are not needed to be corrected. At this time, the correction part 37 does not correct the irradiation parameters stored in the storage part 32. For example, in response to a difference value between the neutron dosage rate and the preset neutron dosage rate calculated by the calculation part 35 being greater than a preset first threshold, or in response to a difference value between the real-time neutron flux rate and the preset neutron flux rate calculated by the calculation part 35 being greater than a preset first threshold, or in response to a difference value between a real-time boron concentration and the preset boron concentration calculated by the calculation part 35 being greater than a preset first threshold, or in response to a difference value between the corrected remaining irradiation time and the remaining irradiation time (a difference value between the preset irradiation time and an actually implemented irradiation time or the last corrected remaining irradiation time) calculated by the calculation part 35 being greater than a preset first threshold, or in response to the calculation part 35 obtaining by comparison that the real-time neutron dosage rate or the real-time neutron flux rate or the real-time boron concentration is greater than a preset second threshold or less than a preset third threshold.

Before the preset irradiation parameters are corrected, the storage part 32 stores the preset irradiation parameters, and the display part 38 displays the remaining irradiation time and other preset irradiation parameters in real time. After the preset irradiation parameters are corrected, the storage part 32 stores a latest set of corrected irradiation parameters, and the display part 38 displays the corrected remaining irradiation time and a latest set of other corrected irradiation parameters in real time. The display part 38 also displaying which irradiation parameters besides the remaining irradiation time, may be selected according to actual needs. The display part 38 may display irradiation parameters, and may also display a part of the irradiation parameters. Usually, the display part 38 displays information such as the remaining irradiation time, the real-time irradiation dosage, the boron concentration, or the like.

In the embodiments disclosed in the disclosure, the calculation part 35 combines the real-time neutron dosage $D_r$ detected by the neutron dosage detection device 21 and the preset neutron dosage $D_{total}$ input by the input part 31, to obtain the corrected remaining irradiation time $t_r$ by calculation. Here to is the preset irradiation time, t is the real-time irradiation time detected by the detection system, that is, an implemented irradiation time, D is an average neutron dosage value in a period oft, and P is a percentage of the real-time neutron dosage to the preset neutron dosage. P is calculated by using a formula (2-1):

$$P = \frac{D_r}{D_{total}} \cdot 100\% \qquad (2\text{-}1)$$

When P is less than 97%, the corrected remaining irradiation time $t_r$ is calculated by using a formula (2-2) and a formula (2-3):

$$\overline{D} = \frac{D_r}{t} \qquad (2\text{-}2)$$

$$t_r = \frac{D_{total} - D_r}{\overline{D}} \qquad (2\text{-}3)$$

At this time, the correction part 37 is needed to correct the preset irradiation time or the corrected remaining irradiation time stored in the storage part 32.

When P is greater than or equal to 97%, the correction part 37 adjusts the neutron dosage rate to a first neutron dosage rate less than the preset neutron dosage rate and increases the irradiation time correspondingly, to prevent the sick body S from absorbing excessive neutrons. The first neutron dosage rate is $\frac{1}{7}$ to $\frac{1}{2}$ of the preset neutron dosage rate. Further, the neutron dosage rate is adjusted to $\frac{1}{5}$ of the preset neutron dosage rate $I_d$, that is, the first neutron dosage rate is equal to $I_d/5$, and the corrected remaining irradiation time $t_r$ is calculated by using a formula (2-4):

$$t_r = \frac{D_{total} - D_I}{\frac{I_d}{5}} \qquad (2\text{-}4)$$

At this time, the correction part 37 is needed to modify the remaining irradiation time and the preset neutron dosage rate in the storage part 32 to the corrected remaining irradiation time $t_r$ and the corrected neutron dosage rate respectively, and the control part 33 performs the therapy plan according to the corrected irradiation parameters. In other implementations, the neutron dosage rate may be adjusted to other multiples, such as $\frac{1}{3}$, $\frac{1}{4}$, $\frac{1}{6}$, $\frac{1}{7}$, or the like, of the preset neutron dosage rate, to prevent the sick body S from absorbing excessive neutrons under irradiation of the neutron beam with a high neutron dosage rate. Furthermore, the correction part 37 may adjust the neutron dosage rate when P is greater than or equal to 90%, or greater than or equal to 95%, or greater than or equal to other ratios, and the ratio may be preset according to actual situations. Of course, whether the neutron dosage rate is needed to be adjusted to the first neutron dosage rate less than the preset neutron dosage rate may also be determined without the value of P calculated by the calculation part 35, instead after a condition where the neutron dosage rate is needed to be corrected at what percentage of the real-time neutron dosage to the preset neutron dosage based on the preset neutron dosage is determined, a threshold is manually set and input into the storage part 32 through the input part 31 for storage. When the detected real-time neutron dosage is greater than or equal to the threshold, the determination part 36 determines that the irradiation parameters are needed to be corrected, and the correction part 37 is enabled to adjust the neutron dosage rate to be the first neutron dosage rate less than the preset neutron dosage rate.

In the above embodiments, when P is less than 97%, the calculation unit 35 calculates an irradiation time needed to complete irradiation with the preset neutron dosage on the premise of keeping the real-time neutron dosage rate unchanged. In other implementations, the purpose of completing the irradiation with the preset dosage within the preset irradiation time is achieved by changing the neutron dosage rate or the boron concentration while keeping the irradiation time unchanged. Methods for changing the neutron dosage rate include changing power of the accelerator, changing thickness of the target layer of the target 112, or the like. The corrected neutron dosage rate $I_r$ is calculated by using a formula (2-5):

$$I_r = \frac{D_{total} - D_I}{t_0 - t} \tag{2-5}$$

Since the neutron dosage rate is calculated from the neutron flux rate through the conversion factor, and the neutron flux rate is obtained by integrating the neutron counting rate, the corrected neutron dosage rate is equivalent to the corrected neutron flux rate and the neutron counting rate.

In the implementation, when P is greater than or equal to 97%, in order to prevent the sick body S from absorbing excessive neutrons under irradiation of the neutron beam with a high neutron dosage rate, the neutron dosage rate is still adjusted to $\frac{1}{5}$ of the preset neutron dosage rate, and the corrected remaining irradiation time $t_r$ is calculated by using the formula (2-4).

When the actually implemented irradiation time reaches the preset irradiation time, or when the actually irradiated neutron dosage reaches the preset neutron dosage, the control part sends, to the neutron capture therapy device, an instruction of stopping irradiation.

The monitoring system 3 is provided with the correction part 37 which corrects the irradiation parameters stored in the storage part 32 and configured to perform the therapy plan, therefore it is ensured that the neutron dosage of the neutron beam irradiated to the sick body is basically consistent with the preset neutron dosage, and accuracy of the neutron dosage of the neutron beam irradiated to the sick body S is further improved. Furthermore, when the percentage of the real-time neutron dosage to the preset neutron dosage is greater than or equal to 97%, the neutron dosage rate is reduced and the irradiation time is correspondingly increased, to prevent the sick body S from absorbing excessive neutrons under irradiation of the neutron beam with a high neutron dosage rate, which also has an effect of improving accuracy of the neutron dosage of the neutron beam irradiated to the sick body S.

In the implementations listed above, it may be determined, according to the real-time neutron dosage obtained by the neutron dosage detection device 21, whether the preset irradiation parameters are needed to be corrected, and the corrected irradiation parameters are calculated according to the real-time irradiation parameters and the preset irradiation parameters. In other implementations, it may be determined, according to the real-time irradiation parameters detected by the temperature detection device 22, the displacement detection device 23 or the boron concentration detection device, whether the preset parameters are needed to be corrected, and the corrected irradiation parameters are calculated according to the real-time irradiation parameters detected by these detection devices. For example, when the boron concentration detection device detects that the boron concentration in the body of the sick body S is inconsistent with the preset boron concentration or does not fall within a preset range, the correction part 37 corrects the remaining irradiation time or corrects a rate of delivering boron into the body of the sick body. Usually, it is difficult to correct the boron concentration in the body of the sick body S in a short period of time when the irradiation therapy is closer to the end. At this time, the remaining irradiation time is usually selected to be corrected.

Accuracy of the irradiation dosage of the neutron beam is needed in a practical therapy. Excessive irradiation dosages may cause potential harm to the sick body S, and too few irradiation dosages may reduce quality of therapy. Both a calculation error in calculation of the preset neutron dosage, and a deviation between the real-time irradiation parameter and the preset irradiation parameter during actual irradiation may cause inaccurate neutron irradiation dosage. Therefore, in addition to the real-time corrected irradiation parameters, calculation of the preset irradiation parameters is also needed during the actual irradiation. Therefore, the correction system is needed to correct the preset neutron dosage, to ensure that the neutron irradiation dosage applied to the sick body S is more accurate. When the preset neutron dosage of the neutron beam is corrected, the influence of factors such as a positioning deviation of the sick body S, a real-time neutron dosage rate deviation, the boron concentration in the body of the sick body, the neutron flux, or the like, should be considered.

A correction coefficient used by the correction system includes a neutron correction coefficient $K_1$ and a boron correction coefficient $K_2$. Here the neutron correction coefficient $K_1$ is related to a positioning correction coefficient $K_p$ and a neutron beam intensity correction coefficient $K_i$. The boron correction coefficient $K_2$ is related to a boron concentration correction coefficient $K_b$ and a boron self-shielding effect correction coefficient $K_s$.

A deviation between the real-time neutron dosage rate and the preset neutron dosage rate may directly cause a deviation of the neutron dosage irradiated to the sick body. Therefore, the positioning correction coefficient $K_p$ and the neutron beam intensity correction coefficient $K_i$ are introduced to correct the neutron irradiation dosage.

The self-shielding effect means that when there is a different boron concentration, a track of the neutron beam irradiated into a tumor part is also different. The higher the boron concentration in the body of the sick body S, the poorer the penetrating capability of the neutron beam, the shorter the track of the neutron beam irradiated into the tumor, and thus the neutron beam may react with boron in a shallower track. On the contrary, the longer the track of the neutron beam irradiated into the tumor, and thus the neutron beam may react with boron in a deeper track. A first boron concentration value in the body of the sick body is obtained by the boron concentration detection device, a first track of the neutron beam irradiated into the tumor part is provided, and the correction system obtains a first boron correction coefficient. A second boron concentration value in the body of the sick body is obtained by the boron concentration detection device, a second track of the neutron beam irradiated into the tumor part is provided, and the correction system obtains a second boron correction coefficient. Here the first boron concentration value is greater than the second boron concentration value, the first track is less than the second track, and the first boron correction coefficient is less than the second boron correction coefficient. Therefore, when the neutron irradiation dosage is calculated, the influence of the self-shielding effect on an actual irradiation effect of the neutron beam and the irradiation track of the neutron beam should be considered, thus the boron concentration correction coefficient $K_b$ and the boron self-shielding effect correction coefficient $K_s$ are introduced to correct the neutron irradiation dosage.

The neutron correction coefficient $K_1$, the positioning correction coefficient $K_p$ and the neutron beam intensity correction coefficient $K_i$ are calculated by using a formula (3-1), a formula (3-2) and a formula (3-3) respectively, and the relevant formulas are as follows.

$$K_1 = K_p \cdot K_i \qquad (3\text{-}1)$$

$$K_p = \frac{D}{D_0} \qquad (3\text{-}2)$$

$$K_i = \frac{I}{I_0} \qquad (3\text{-}3)$$

where D is an actual therapy dosage, that is, the real-time neutron dosage $D_r$ measured by the neutron dosage detection device 21;

$D_0$ is an uncorrected preset neutron dosage;

I is an actual neutron beam intensity, that is, the real-time neutron dosage rate measured by the neutron dosage detection device 21; and $I_0$ is a theoretical beam intensity, that is, the preset neutron dosage rate input by the input part 31.

The boron correction coefficient $K_2$, the boron concentration correction coefficient $K_b$ and the boron self-shielding effect correction coefficient $K_s$ are calculated by using a formula (3-4), a formula (3-5) and a formula (3-6) respectively, and the relevant formulas are as follows.

$$K_2 = K_b \cdot K_S \qquad (3\text{-}4)$$

$$K_b = \frac{B}{B_0} \qquad (3\text{-}5)$$

$$K_S = \frac{\varphi_B}{\varphi_{B0}} \qquad (3\text{-}6)$$

where B is an actual boron concentration in the body of the sick body S, that is, the real-time boron concentration detected by the boron concentration detection device;

$B_0$ is a boron concentration set value in the therapy plan, that is, the preset boron concentration input by the input part 31;

$\varphi_B$ is a thermal neutron flux in the body of the sick body S when a boron concentration distribution is B; and $\varphi_{B0}$ is a thermal neutron flux in the body of the sick body S when a boron concentration distribution is $B_0$.

The uncorrected preset neutron dosage $D_0$ is calculated by using a formula (3-7) as follows.

$$D_{eq} = D_B \cdot B_{con} \cdot CBE + D_f \cdot RBE_n + D_{th} \cdot RBE_n + D_r \cdot RBE_r \qquad (3\text{-}7)$$

The corrected preset neutron dosage $D_{total}$ in the therapy plan is calculated by using a formula (3-8) as follows.

$$D_{total} = K_1 \cdot (K_2 \cdot D_B \cdot B_{con} \cdot CBE + D_f \cdot RBE_n + D_{th} \cdot RBE_n + D_r \cdot RBE_r) \qquad (3\text{-}8)$$

where $D_B$ is a dosage at the boron concentration of 1 ppm, and has a unit Gy;

$B_{con}$ is an actually measured boron concentration, and has a unit ppm;

$D_f$ is a fast neutron dosage, and has a unit Gy;

$D_{th}$ is a thermal neutron dosage, and has a unit Gy;

$RBE_n$ is a Relative Biological Effectiveness (RBE) of the neutron;

$D_r$ is a gamma dosage, and has a unit Gy; and $RBE_r$ is a gamma RBE.

During actual therapy, the correction system corrects a preset neutron dosage in a pre-formulated therapy plan, so as to prevent applying an inaccurate neutron dosage to the sick body S.

The correction system comprehensively considers the influence of factors such as the positioning deviation of the sick body S, the real-time neutron dosage rate deviation, the real-time boron concentration, or the like on the preset neutron dosage, and introduces the neutron correction coefficient $K_1$ and the boron correction coefficient $K_2$ to correct the preset neutron dosage, so that accuracy of the neutron dosage of the neutron beam irradiated to the sick body S is ensured from the source.

During actual therapy, after the input part 31 completes input of the preset irradiation parameters, an operator starts the neutron capture therapy device to perform irradiation therapy. After irradiation begins, the input function of the input part 31 is locked, and relevant irradiation parameters may not be input again, thus it may be ensured that a situation where wrong parameters and instructions are input due to accidental touch or error operation during irradiation may be prevented. However, when the therapy process is slightly inconsistent with an ideal state, irradiation may be stopped or continued according to the abnormal state, and parameters may not be corrected in time or instructions may not be changed in time during irradiation. However, when an operation interface is simply set to be operated in real time, irradiation parameters and control instructions may still be input by the input part 31 after irradiation begins, thus it may be ensured that correct irradiation parameters and instructions may be input in real time during irradiation. However, there is still a risk that the irradiation result is affected by inputting wrong parameters and instructions or repeatedly inputting operation instructions due to error operation during irradiation.

Figure 7:
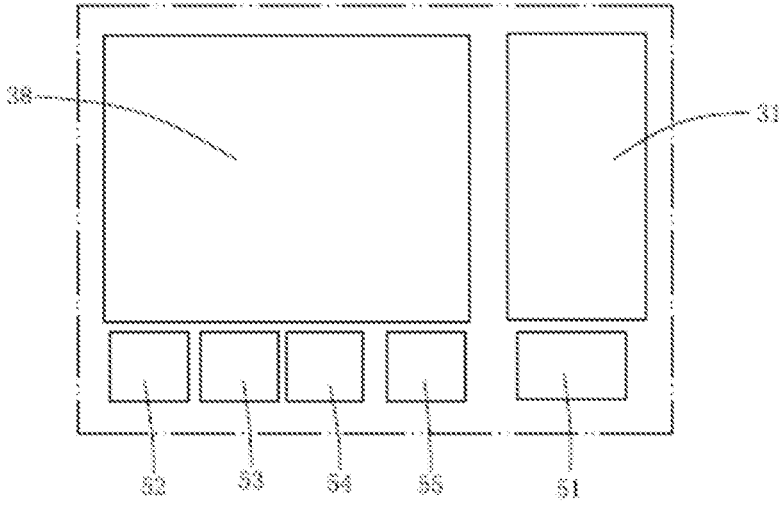
FIG. 7 is a schematic diagram of an anti-misoperation system in combination with a display part and an input part of a neutron capture therapy device of the disclosure.

As shown with reference to FIG. 7, the neutron capture therapy device is provided with a control interface. The control interface includes the above input part 31, the display part 38, an errorless information confirmation button 51, an irradiation beginning button 52, an irradiation pause button 53, an irradiation cancel button 54 and a report generation button 55. An operator activates the errorless information confirmation button 51 to transmit, to the monitoring system 3, a signal that information has been confirmed to be errorless. After the monitoring system 3 receives the signal that information has been confirmed to be errorless, a condition for starting the neutron capture therapy device for neutron beam irradiation is met. After the monitoring system 3 receives the signal that information has been confirmed to be errorless, the irradiation beginning button 52 is activated, and a sufficient condition for starting the neutron capture therapy device for neutron beam irradiation is met. After the neutron capture therapy device is started, the neutron beam irradiation may be paused by the irradiation pause button 53, and the neutron beam irradiation may be cancelled by the irradiation cancel button 54. After irradiation is completed, the report generation button 55 may be activated to automatically generate a report related to the irradiation therapy. When the neutron beam irradiation is paused, it means that the irradiation parameters and instructions are kept unchanged. By activating the irradiation beginning button 52 again, the neutron beam irradiation is performed with original irradiation parameters and instructions. When the neutron beam irradiation is cancelled, it means that the irradiation parameters and instructions are cleared. When the neutron beam irradiation is performed again, the irradiation parameters and instructions are needed to be input again, and the errorless information confirmation button 51 and the irradiation beginning button 52 are activated in sequence.

The anti-misoperation system comprehensively considers two factors of operability and safety, and is provided with a secondary confirmation part and a fool-proofing part to ensure safe and precise irradiation, while the system does not lack real-time operability. Before the operator activates the secondary confirmation part to transmit, to the neutron capture therapy device, the signal that information has been confirmed to be errorless, the neutron capture therapy device may not be started to perform the irradiation therapy plan, that is, the irradiation beginning button 52 may not be started. During starting of the fool-proofing part, the input part 31 which may modify and input the irradiation parameters and instructions and the report generation button 55 are locked.

In the embodiments disclosed in the disclosure, the secondary confirmation part is the errorless information confirmation button 51 on the control interface. Before a doctor starts a program to perform the therapy plan, relevant information is needed to be confirmed twice. After the operator confirms that the input is errorless, and clicks the errorless information confirmation button 51 to input, to the monitoring system 3, an instruction that the information is confirmed to be errorless, the device may be started to perform the therapy plan, thereby reducing the risk of wrongly inputting wrong control instructions due to error operation. For example, before performing irradiation therapy on the sick body S, the doctor should check information of the sick body (such as name, gender, age, or the like), irradiation parameters (such as the irradiation dosage, the collimator number, or the like), or the like. After checking that information is correct, an irradiation beginning function may be activated by clicking the errorless information confirmation button 51 on the control interface. Otherwise, even though the doctor clicks the irradiation beginning button 52, the device refuses to start neutron beam irradiation and gives a prompt that information is not confirmed.

In the embodiments disclosed in the disclosure, the fool-proofing part is the irradiation beginning button 52. After the irradiation beginning button 52 starts the therapy plan, the input function of the input part 31 is locked and any information may not be input. Before irradiation therapy, relevant instructions and irradiation parameters are input by the input part 31. After relevant irradiation parameters and instructions are input into the monitoring system 3, the operator checks whether the relevant irradiation parameters and instructions are correct. After confirming that the relevant irradiation parameters and instructions are correct, the operator activates the errorless information confirmation button 51, the input part 31 may be locked, and the relevant irradiation parameters and instructions may not be modified or added through the input part 31, so as to prevent wrong input. The relevant irradiation parameters and instructions may be input again after the input part 31 is unlocked. In the embodiments disclosed in the disclosure, after the irradiation pause button 53 or the irradiation cancel button 54 is clicked, the irradiation therapy is stopped. At the same time, the input part 31 configured to input relevant information is unlocked, and the relevant information may be modified or added through the input part 31. Of course, the input part may be automatically unlocked after the irradiation therapy is completed. In this way, wrong input is prevented, while operability of the system is ensured. For example, after checking that information of the sick body S, the irradiation parameters and other information are correct, the medical staff clicks the errorless information confirmation button 51 on the control interface, and clicks the irradiation beginning button 52. The system starts the irradiation therapy. At this time, the input part 31 configured to input the relevant information is locked, and input of information may not be performed.

Before the irradiation therapy is completed, the report generation button 55 is also locked, and after the irradiation therapy is completed, the report generation button 55 may be automatically unlocked, that is, the therapy report generation function may be enabled.

The fool-proofing part is not limited to being applied to the irradiation beginning button 52 in the above embodiment, and is also suitable for other buttons and parameter input windows. Furthermore, a carrier for realizing the secondary confirmation and button fool-proofing may be software or hardware, for example, the fool-proofing part may also be a key or a dial switch on a control panel. Before the key or the switch is turned on, certain operations may not be performed, and when the key or the switch is turned on, relevant operations may be performed.

In the embodiments disclosed in the disclosure, instructions and irradiation parameters are input by means of a touch screen. In other implementations, a key (for example, a mechanical key) may be used for input.

The anti-misoperation system may not ensure functions of setting parameters and inputting control instructions if necessary, but also reduce wrong input of parameters or repeated input of instructions due to error operation or other reasons, thereby reducing the risk of operation of the device.

In the neutron capture therapy device of the disclosure, the neutron dosage detection device 21 is provided with at least two counting rate channels with different sensitivities of detecting the neutron, i.e., the first counting rate channel 201 and the second counting rate channel 202, and the counting rate channel selection unit 216 which selects a more accurate counting rate according to an actual situation, to calculate the neutron dosage, so that a counting rate loss error caused by the pulse resolution time may be avoided. At the same time, a statistical error caused by a low counting rate is considered, so that accuracy of real-time neutron dosage detection is improved, thereby improving accuracy of the neutron dosage of the neutron beam irradiated to the sick body S. Furthermore, the neutron dosage detection device 21 is also provided with a counting rate correction unit 217 which may calculate the pulse resolution time of the detector 211, and may calculate the counting rate correction factor according to the pulse resolution time, so that a counting rate error caused by the pulse resolution time is corrected, accuracy of real-time neutron dosage detection is further improved, and accuracy of the neutron dosage of the neutron beam irradiated to the sick body S is further improved.

The neutron capture therapy device of the disclosure is also provided with the monitoring system 3. The monitoring system 3 is provided with the correction part 37 which periodically corrects the irradiation parameters stored in the storage part 32 and configured to perform the therapy plan, therefore it is ensured that the neutron dosage of the neutron beam irradiated to the sick body S is basically consistent with the preset neutron dosage, and accuracy of the neutron dosage of the neutron beam irradiated to the sick body S is further improved. Furthermore, when the percentage of the real-time neutron dosage to the preset neutron dosage is greater than or equal to 97%, the neutron dosage rate is reduced and the irradiation time is correspondingly increased, to prevent the sick body S from absorbing excessive neutrons under irradiation of the neutron beam with a high neutron dosage rate, which also has an effect of improving accuracy of the neutron dosage of the neutron beam irradiated to the sick body S.

The neutron capture therapy device of the disclosure is also provided with the correction system. The correction system comprehensively considers the influence of factors such as the positioning deviation of the sick body S, the real-time neutron dosage rate deviation, the real-time boron concentration, or the like on the preset neutron dosage, and introduces the neutron correction coefficient $K_1$ and the boron correction coefficient $K_2$ to correct the preset neutron dosage, so that accuracy of the neutron dosage of the neutron beam irradiated to the sick body S is ensured from the source.

In conclusion, the neutron capture therapy device of the disclosure may apply an accurate neutron beam irradiation dosage to the sick body and reduce the risk of operation of the device caused by error operation on the premise of ensuring operability of the device.

The neutron capture therapy device disclosed in the disclosure is not limited to contents described in the above embodiments and structures shown in the drawings. Apparent change, substitution or modification made for materials, shapes and positions of components therein on the basis of the disclosure fall within the scope of protection of the disclosure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and might be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A neutron capture therapy apparatus, configured to irradiate a neutron beam with a preset neutron dosage to an object to be irradiated, the neutron beam entering the object to be irradiated and undergoing a nuclear reaction with boron in the object to be irradiated, and the neutron capture therapy apparatus comprising:

a correction system configured to correct the preset neutron dosage; and a detection system, comprising a neutron dosage detection device configured to detect a dosage of the neutron beam in real time and a boron concentration detection device configured to detect a boron concentration in the object to be irradiated, wherein correction coefficients used by the correction system comprise a boron self-shielding effect correction coefficient $K_s$ calculated by using a formula (3-6);

$$K_S = \frac{\varphi_B}{\varphi_{B0}} \tag{3-6}$$

where $\varphi_B$ is a thermal neutron flux in the object to be irradiated when a boron concentration distribution is B, and $\varphi_{B0}$ is a thermal neutron flux in the object to be irradiated when a boron concentration distribution is $B_0$.

2. The neutron capture therapy apparatus of claim 1, wherein the correction system corrects the preset neutron dosage according to a real-time boron concentration and a neutron flux in the object to be irradiated.

3. The neutron capture therapy apparatus of claim 1, wherein the correction coefficients further comprise a positioning correction coefficient $K_p$ calculated by using a formula (3-2):

$$K_p = \frac{D}{D_0} \tag{3-2}$$

where D is a real-time neutron dosage measured by the neutron dosage detection device, and $D_0$ is an uncorrected preset neutron dosage.

4. The neutron capture therapy apparatus of claim 3, wherein the correction coefficients further comprise a neutron beam intensity correction coefficient $K_i$ calculated by using a formula (3-3):

$$K_i = \frac{I}{I_0} \tag{3-3}$$

where I is a real-time neutron dosage rate measured by the neutron dosage detection device, and $I_0$ is a theoretical beam intensity.

5. The neutron capture therapy apparatus of claim 4, wherein the correction coefficients further comprise a boron concentration correction coefficient $K_b$ calculated by using a formula (3-5):

$$K_b = \frac{B}{B_0} \tag{3-5}$$

where B is a real-time boron concentration detected by the boron concentration detection device, and $B_0$ is a boron concentration set value in a therapy plan.

6. The neutron capture therapy apparatus of claim 5, wherein the correction coefficients comprise a neutron correction coefficient $K_1$ and a boron correction coefficient $K_2$ calculated by using a formula (3-1) and a formula (3-4) respectively:

$$K_1 = K_p \cdot K_i \tag{3-1}$$

$$K_2 = K_b \cdot K_S \tag{3-4}.$$

7. The neutron capture therapy apparatus of claim 6, wherein a corrected preset neutron dosage $D_{total}$ is calculated by using a formula (3-8) as follows:

$$D_{total} = K_1 \cdot (K_2 \cdot D_B \cdot B_{con} \cdot CBE + D_f \cdot RBE_n + D_{th} \cdot RBE_n + D_r \cdot RBE_r) \tag{3-8}$$

where $D_B$ is a dosage at the boron concentration of 1 ppm and has a unit Gy, $B_{con}$ is an actually measured boron concentration and has a unit ppm, $D_f$ is a fast neutron dosage and has a unit Gy, $D_{th}$ is a thermal neutron dosage and has a unit Gy, $RBE_n$ is a Relative Biological Effectiveness (RBE) of the neutron, $D_r$ is a gamma dosage and has a unit Gy, and $RBE_r$ is a gamma RBE.

8. The neutron capture therapy apparatus of claim 1, wherein a first boron concentration value in the object to be irradiated is obtained by the boron concentration detection device, and a first boron self-shielding effect correction coefficient is obtained by the correction system; a second boron concentration value in the object to be irradiated is obtained by the boron concentration detection device, and a second boron self-shielding effect correction coefficient is obtained by the correction system, and wherein the first boron concentration value is greater than the second boron concentration value, and the first boron self-shielding effect correction coefficient is less than the second boron self-shielding effect correction coefficient.

\* \* \* \* \*